United States Patent

Houle et al.

[11] Patent Number: 5,261,900
[45] Date of Patent: * Nov. 16, 1993

[54] REUSABLE DIAPER

[75] Inventors: Christine B. Houle, 11240 240th St., Scandia, Minn. 55073; Joanne K. Callahan, Scandia, Minn.

[73] Assignee: Christine B. Houle, Scandia, Minn.

[*] Notice: The portion of the term of this patent subsequent to Oct. 29, 2008 has been disclaimed.

[21] Appl. No.: 782,309

[22] Filed: Oct. 24, 1991

Related U.S. Application Data

[63] Continuation-in-part of Ser. No. 558,100, Jul. 26, 1990, Pat. No. 5,061,260.

[51] Int. Cl.$^5$ ............................................. A61F 13/15
[52] U.S. Cl. ................................. 604/385.1; 604/378; 604/358
[58] Field of Search ............. 604/355, 358, 378, 385.1

[56] References Cited

U.S. PATENT DOCUMENTS

| | | | |
|---|---|---|---|
| 401,123 | 5/1943 | Van Den Bergh | 604/358 |
| 2,145,137 | 1/1939 | Sayers | 604/358 |
| 2,600,634 | 6/1952 | Gannon | 604/358 |
| 2,681,062 | 6/1954 | Nichols | 604/358 |
| 3,409,012 | 11/1968 | Seltzer | 604/378 |
| 3,868,287 | 2/1975 | Lewyckyj | 604/358 |
| 4,772,281 | 9/1988 | Armstead | 304/358 |
| 5,061,260 | 10/1991 | Callahan et al. | 604/378 |

FOREIGN PATENT DOCUMENTS

| | | | |
|---|---|---|---|
| 0329858 | 8/1989 | European Pat. Off. | 604/358 |
| 0691029 | 5/1940 | Fed. Rep. of Germany | 604/358 |
| 1015306 | 9/1952 | France | 604/358 |
| 0660386 | 2/1964 | Italy | 604/358 |
| 0692444 | 7/1965 | Italy | 604/358 |
| 0048802 | 1/1988 | Japan | 604/358 |
| 0123412 | 11/1927 | Switzerland | 604/358 |
| 0294498 | 1/1954 | Switzerland | 604/358 |
| 0431420 | 8/1967 | Switzerland | 604/358 |
| 2132897 | 7/1984 | United Kingdom | 604/358 |
| 2189705 | 11/1987 | United Kingdom | 604/358 |

*Primary Examiner*—Randall L. Green
*Assistant Examiner*—Gina M. Gualtieri
*Attorney, Agent, or Firm*—Merchant, Gould, Smith, Edell, Welter & Schmidt

[57] ABSTRACT

The present invention provides a nondisposable diaper comprising at least three layers. In one embodiment, continuous perimeter closure is provided between at least two of the layers and discontinuous perimeter closure is provided between at least two of the layers. In other embodiments, continuous or discontinuous perimeter closure is provided between all the layers.

8 Claims, 5 Drawing Sheets

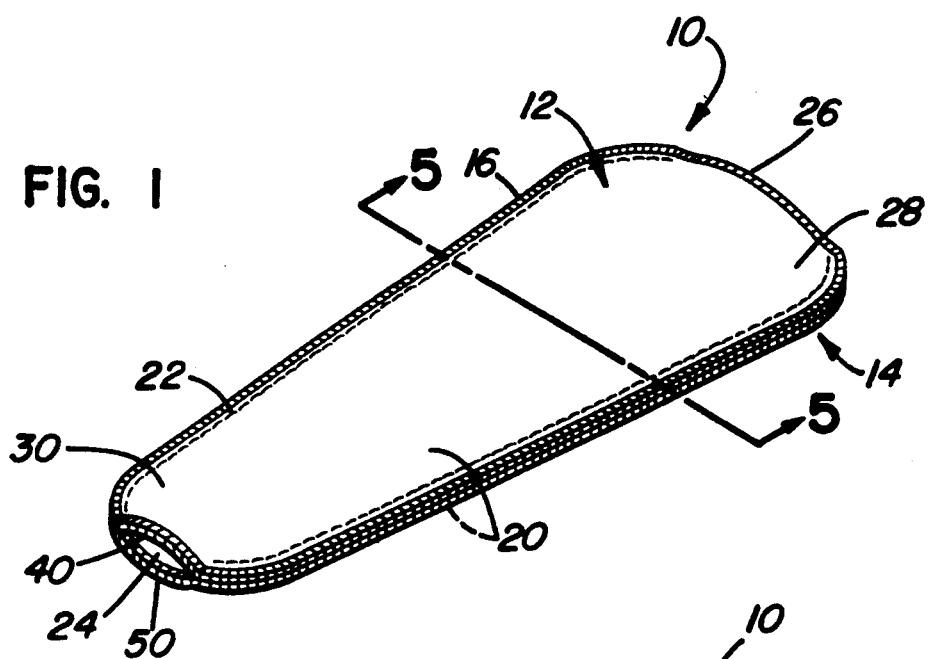
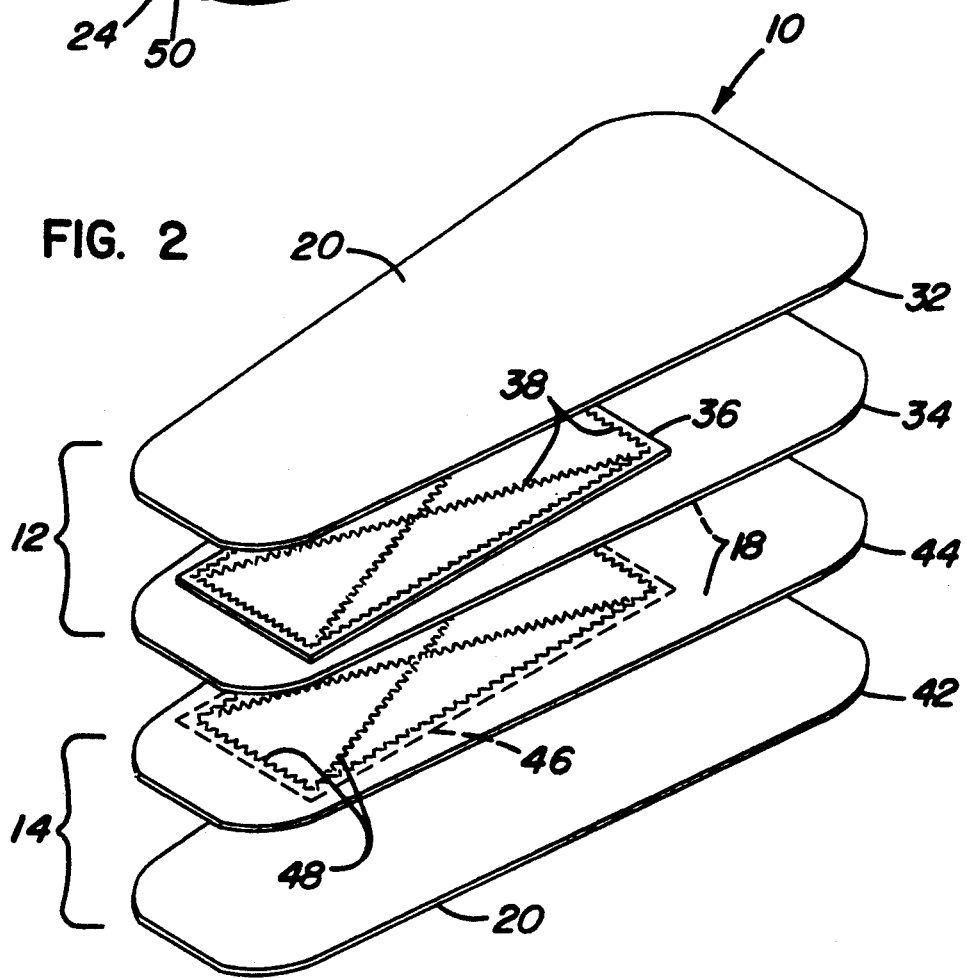

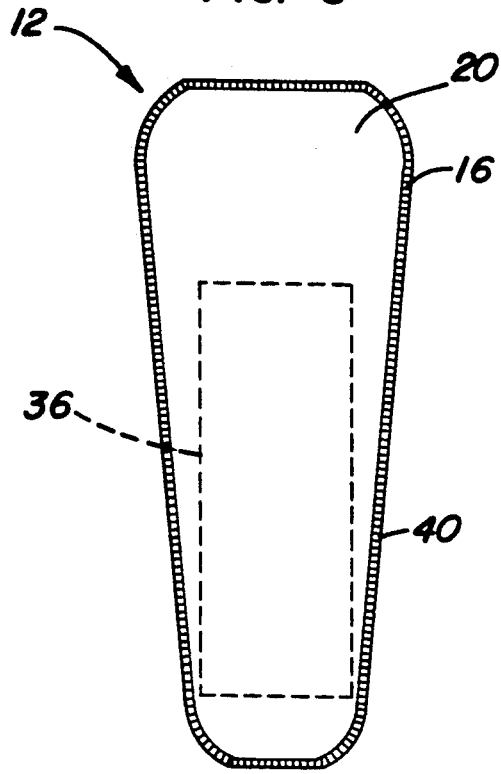
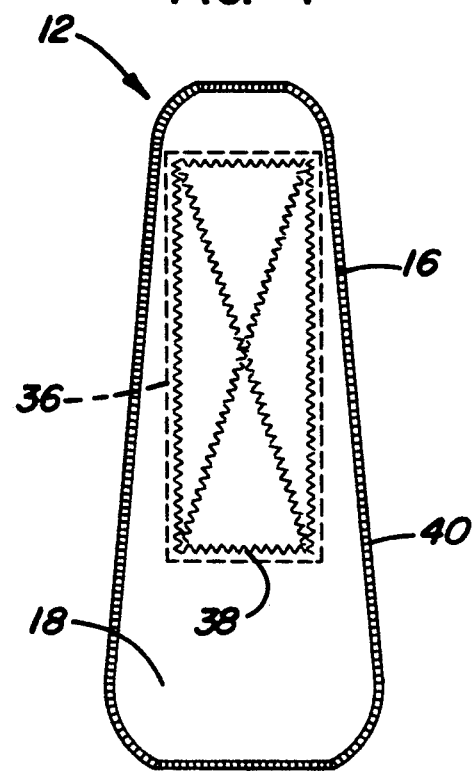
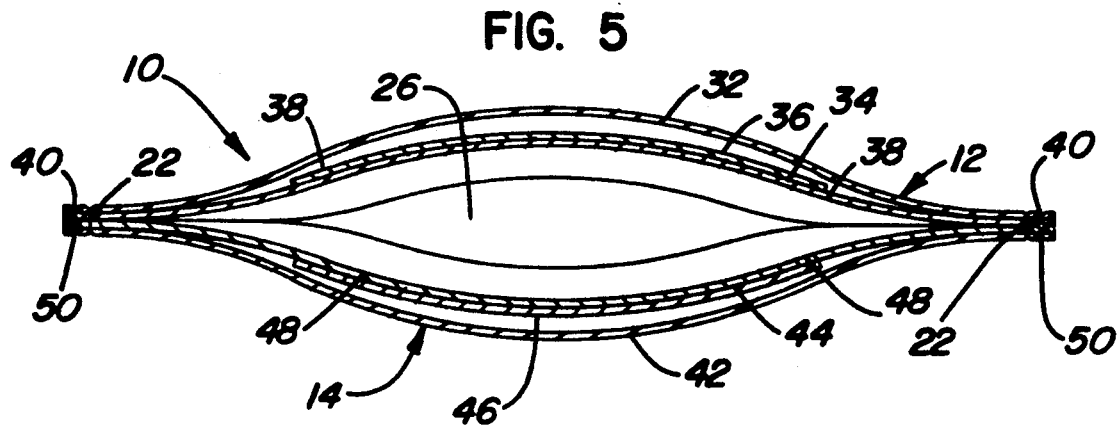

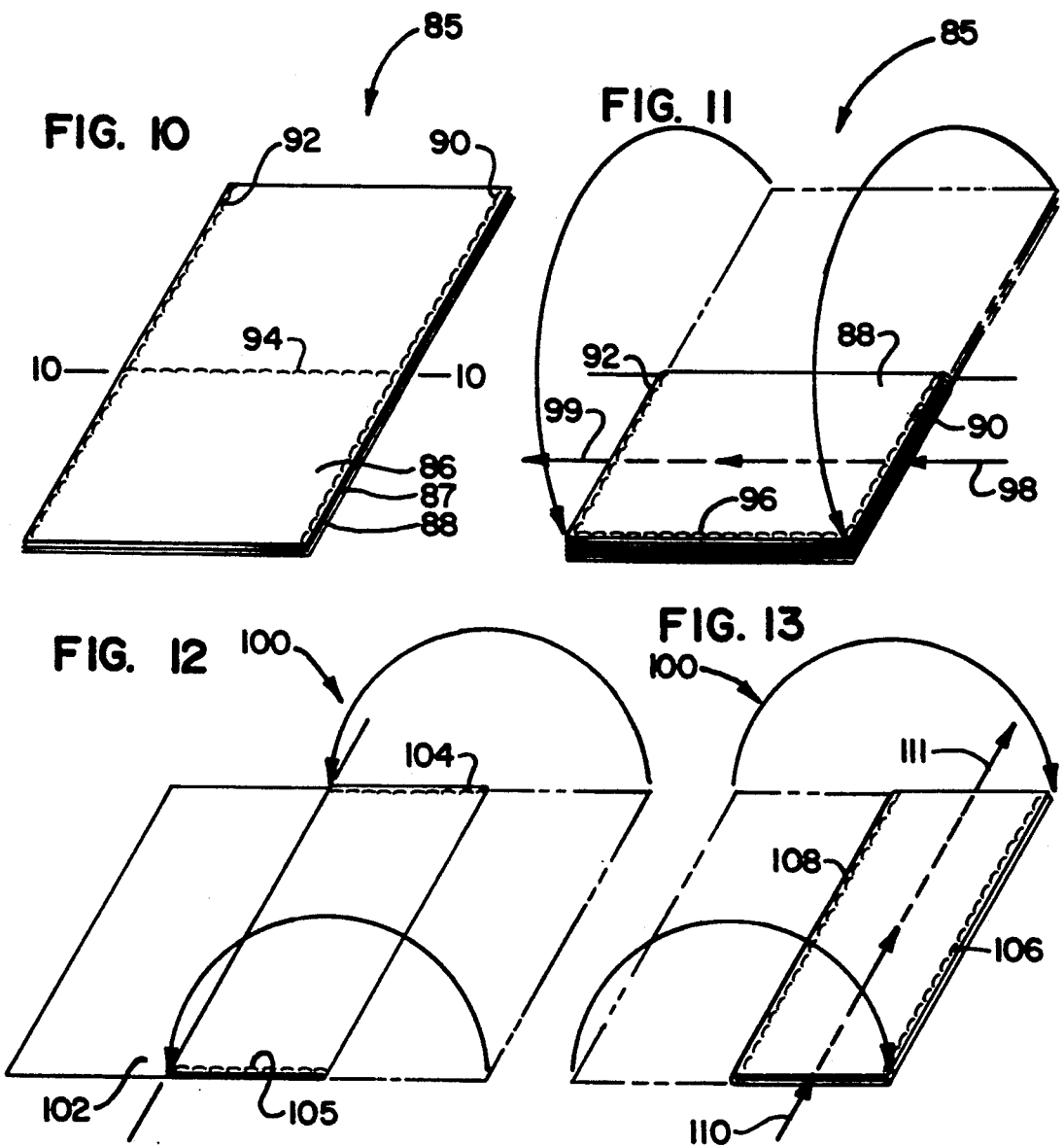

5,261,900

1

REUSABLE DIAPER

This is a continuation-in-part application of application Ser. No. 07/558,100, filed Jul. 26, 1990, now U.S. Pat. No. 5,061,260.

FIELD OF INVENTION

The present invention relates to an improved nondisposable diaper.

BACKGROUND OF THE INVENTION

With the ever present waste management problem, the baby care industry has felt a long and increasing need for new and improved nondisposable diapers. For example, some publications have estimated that approximately 18 billion plastic diapers are buried in landfills each year, and that disposable diapers constitute approximately 30% of the total nonbiodegradable materials buried in landfills in the United States.

Part of the problem is that the baby care industry has made few improvements to enhance the ease of use and durability of the conventional nondisposable diapers. The present invention provides such improvements and accordingly should provide additional encouragement to parents to switch from using disposable diapers, which have created an environmental problem, to a nondisposable diaper.

For example, the present invention provides a nondisposable diaper in which critical stitching is enclosed and thus protected against wear and tear from outside contact. Also, by not exposing such seams to the baby's bottom, the nondisposable diaper in the present invention is more comfortable for the baby. Also, the present invention provides an improved design which permits the nondisposable diaper to dry faster and more efficiently. Decreased drying time translates into energy savings. Also, the nondisposable diaper according to the present invention requires less material which means that more diapers may be washed in one drying load.

A related problem often encountered with conventional nondisposable diapers is that because they do not dry during a typical drying cycle, they remain somewhat damp while stored. A damp diaper is more susceptible to molding and rotting, and thus typically will not last as long. The present invention helps to eliminate these and other problems associated with conventional nondisposable diapers.

SUMMARY OF THE INVENTION

The nondisposable diaper of the present invention includes at least three layers having perimeter ends. Between at least two of the layers, continuous perimeter closure is provided along their respective perimeter ends. Also, between at least two of the layers, discontinuous perimeter closure is provided. The discontinuous perimeter closure defines at least one opening between the layers and thereby permits the diaper to dry faster.

In another embodiment, continuous perimeter closure is provided between all the layers.

In another embodiment, discontinuous perimeter closure is provided between all the layers.

BRIEF DESCRIPTION OF THE DRAWINGS

FIG. 1 is a perspective view of a nondisposable diaper constructed according to the preferred embodiment of the present invention.

FIG. 2 is an exploded perspective view of a nondisposable diaper constructed according to the preferred embodiment of the present invention.

FIG. 3 shows a top view of top section 12 (or its mirror image bottom section 14) shown in FIG. 2.

FIG. 4 is a bottom view of top section 12 (or its mirror image bottom section 14) shown in FIG. 2.

FIG. 5 is a cross-sectional view of the diaper shown in FIG. 1, taken along lines 5—5.

FIG. 8 also shows an independent embodiment of the present invention.

FIG. 10 shows the embodiment depicted in FIG. 11 in a first position comprising three sheets of material.

FIG. 11 shows the three sheets of material shown in FIG. 10 folded to a second position comprising six layers.

FIGS. 12 and 13 show a single sheet of material being folded to provide a three layer construction of an embodiment of the present invention.

DETAILED DESCRIPTION OF THE PREFERRED EMBODIMENTS

Figure 6:
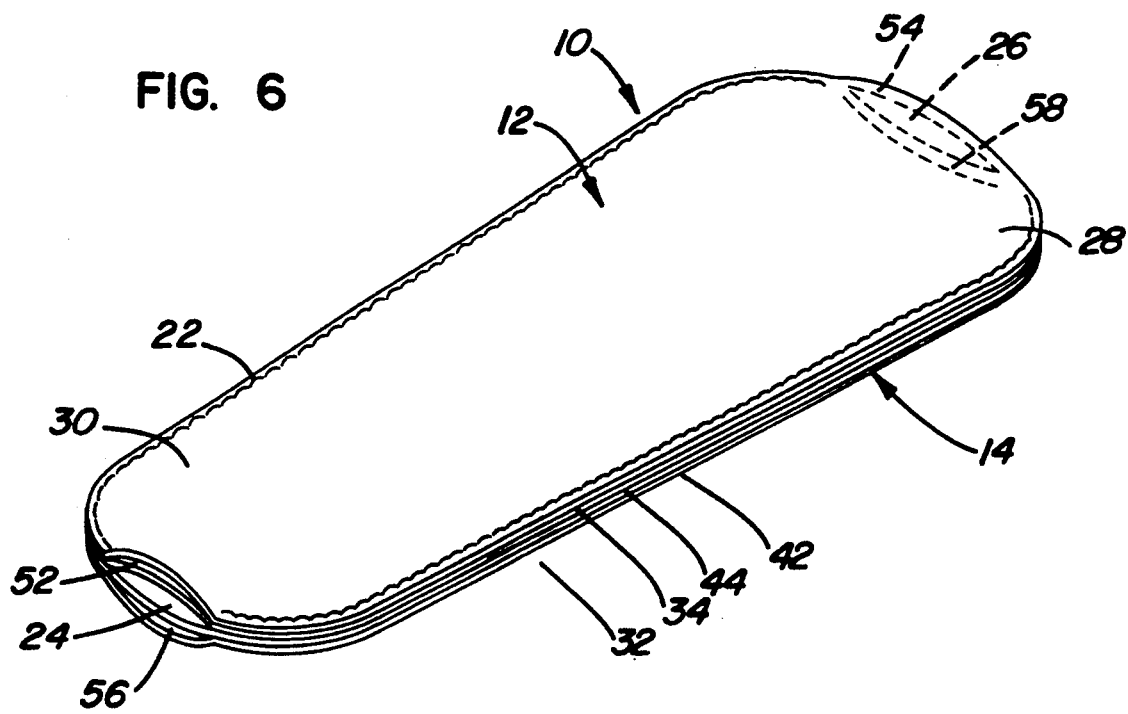
FIG. 6 is an alternative preferred embodiment of the nondisposable diaper shown in FIGS. 1-5.

Referring now to the drawings, FIGS. 1-5 disclose a nondisposable diaper constructed according to the preferred embodiment of the present invention. FIG. 6 discloses an alternative preferred embodiment of the nondisposable diaper shown in FIGS. 1-5. It should be noted that like reference numerals designate corresponding elements throughout the drawings.

Referring to FIGS. 1, 2 and 5, the nondisposable diaper 10 according to the present invention includes a top section 12 and a bottom section 14. In the preferred embodiment, the top and bottom sections 12, 14 are symmetrical, each having corresponding perimeter ends 16 and inside surfaces 18 and outside surfaces 20. The respective inside surfaces of the top and bottom sections face one another.

The nondisposable diaper further includes attachment means 22 for attaching the top section 12 to the bottom section 14 along their respective perimeter ends 16 in a discontinuous manner. The attachment means may comprise discontinuous perimeter stitching 22 as shown in FIGS. 1 and 5. The discontinuous perimeter stitching defines at least one opening 24 between the respective top and bottom sections 12, 14. The opening 24 permits air to more freely enter and flow between the respective inside surfaces 18 of the top and bottom sections during, for example, a drying cycle. This permits the nondisposable diaper 10 to dry faster and more efficiently and thereby helps to eliminate the problem encountered when the diaper does not dry during the typical drying cycle which is used for other clothes.

In the preferred embodiment, the discontinuous perimeter stitching 22 defines first and second openings 24, 26 located at opposite ends of the nondisposable diaper. As shown in the drawings, the nondisposable diaper 10 according to the preferred embodiment comprises a wedge-shaped nondisposable diaper, having a wider end 28 and a narrower end 30, wherein the first opening 24 is located at the wider end 28 and the second opening 26 is located at the narrower end 30. It is noted that the wedged-shaped nondisposable diaper 10 according to the present invention is adapted to be used as an insert within a conventional diaper cover. It should be understood, however, that under the present invention, the diaper could be made in a variety of different shapes, including but not limited to wedged-shaped as shown, or hourglass shaped, rectangular shaped or other shapes adaptable to fit a baby's bottom. Also, the nondisposable diaper according to the present invention need not be an insert; it may be otherwise attachable with pins or other means for securing the diaper to the baby's bottom.

As best shown in FIGS. 2 and 5, the top section 12 further includes a top outside layer 32, a top inside layer 34, and a top absorbency pad 36 located between the top outside and inside layers 32, 34. In the preferred embodiment, the top section 12 further includes first top attachment means 38 for attaching the top absorbency pad 36 to the top inside layer 34. In the preferred embodiment, the first top attachment means 38 is enclosed within the top outside layer and thus protected from wear and tear associated with outside contact to the nondisposable diaper. The first top attachment means preferably comprises stitching 38 as shown in FIGS. 2 and 3. It should be understood that in alternative embodiments, the first attachment means could attach the absorbency pad to the top outside layer and still incorporate patentable features of the present invention. The top section 12 according to the preferred embodiment further includes a second top attachment means 40 for attaching the top outside layer 32 to the top inside layer 34.

The bottom section 14 includes a bottom outside layer 42, a bottom inside layer 44, and a bottom absorbency pad 46 located between the bottom outside and inside layers. The bottom section 14 further includes a first bottom attachment means 48 for attaching the absorbency pad 46 to the bottom inside layer 44, the attachment means being enclosed within the bottom outside layer 42 and thus protected from wear and tear from outside contact. The first bottom attachment means preferably comprises stitching 48 as shown in FIGS. 2. The bottom section 14 according to the preferred embodiment also includes a second bottom attachment means 50 for attaching the bottom outside layer 42 to the bottom inside layer 44.

As shown in FIGS. 2, 3 and 4, the top and bottom absorbency pads are smaller in size than the other layers and are centrally located where added absorbency is needed. It should be noted that the top and bottom absorbency pads 36, 46 need not be located between the respective top and bottom outside and inside layers. For example, in an alternative embodiment, the top and bottom absorbency pads could be attached to the inside surfaces 18 (i.e., the opposite sides of the top and bottom inside layers 34, 44) of the top and bottom sections.

In a preferred embodiment, the second top attachment means 40 and the second bottom attachment means 50 comprise continuous perimeter stitching as shown in FIGS. 1, 3 and 4. In an alternative preferred embodiment shown in FIG. 6, the second top and bottom attachment means 40, 50 and the means for attaching the top section 12 to the bottom section 14 comprise discontinuous perimeter stitching 22 which defines at least three openings: a first opening 24 between the top section 12 and the bottom section 14; a first top opening 52 between the top outside layer 32 and top inside layer 34; a first bottom opening 56 between the bottom outside layer 42 and the bottom inside layer 44. In the preferred embodiment, the discontinuous stitching 22 defines six openings, including the above listing openings: a second opening 26 between the top section 12 and bottom section 14; a second top opening 54 between the top outside layer 32 and the top inside layer 34; and a second bottom opening 58 between the bottom outside layer 42 and the bottom inside layer 44. These openings allow air to more freely flow between the various layers and sections and thereby permit the diaper to dry faster and more efficiently. Each opening should extend at least half the width of the end (i.e., of the wider end 28 or of the narrower end 30) on which the opening is located. This proportion for the openings provides improved dryability of the diaper without jeopardizing the integrity of the diaper's construction. For cost reasons, the manufacturer may, however, prefer to have each opening extend the entire width of the diaper end. It should be understood that the width of the opening may vary.

Several advantages should be noted in the present invention. First, the nondisposable diaper constructed according to the preferred embodiment provides two separate absorbency pads, as opposed to one thicker absorbency pad. This feature facilitates drying. Also, by providing air vents as described above, the absorbency pads are exposed to a more direct air flow.

FIGS. 3 and 4 are identified as top section 12. However, it should be understood that FIGS. 3 and 4 could also be used to describe bottom section 14 because, in the preferred embodiment, bottom section 14 mirrors the top section 12. For convenience, the top section will be referred to but it should be understood that FIGS. 3 and 4 also describe the bottom section 14. FIGS. 3 and 4 show that the absorbency pad 36 is enclosed between the top outside layer 32 and top inside layer 34. As shown, the stitching 38 does not penetrate the top outside layer 32 and therefor is protected against the wear and tear from outside contact. Thus, the critical seams associated with stitching 38 are not exposed for example to the baby's bottom. This feature also makes the nondisposable diaper more comfortable for the baby. Thus, the nondisposable diaper according to the present invention should be more durable and comfortable.

In alternative embodiments of the present invention, the diaper may comprise at least three layers. It should be noted that the term "layer" as used herein does not necessarily mean a single discrete sheet of material. In other words, several (or any number of) layers may be formed from a single sheet of material as shown in FIGS. 7–13. It should be noted that significant labor saving advantages are obtained by using, for example, a single sheet of material to make several layers. For example, on the folded side, additional stitching or attachment means need not be provided to have perimeter closure along the folded side.

It should be noted that in other embodiments of this invention, continuous perimeter closure may be provided between all the layers of diaper.

In the preferred embodiment, between at least two of the layers, continuous perimeter closure means may be provided. Perimeter closure between two layers may be provided by some means of attachment such as stitching, adhesive, velcro, or the like. Perimeter closure may also be provided by a fold in material which provides continuity between the two layers. Perimeter closure may also be provided between two discrete layers by being enclosed within a fold of one of the layers or by being enclosed between two independent layers having a fold which provides continuity. In other words, continuous perimeter closure does not necessarily mean that the two layers are attached around their respective perimeter ends in a continuous manner. Rather, the perimeter ends may be attached or enclosed as discussed above.

Between at least two of the layers, discontinuous perimeter closure may be provided. The phrase "perimeter closure" is defined above. The discontinuous perimeter closure defines at least one opening between the two layers, the opening permitting air to more freely enter and flow between the layers and thereby permit the diaper to dry faster.

It should be noted that in other embodiments, discontinuous perimeter closure may be provided between all the layers of the diaper. See, for example, FIGS. 6 and 8.

Figure 7:
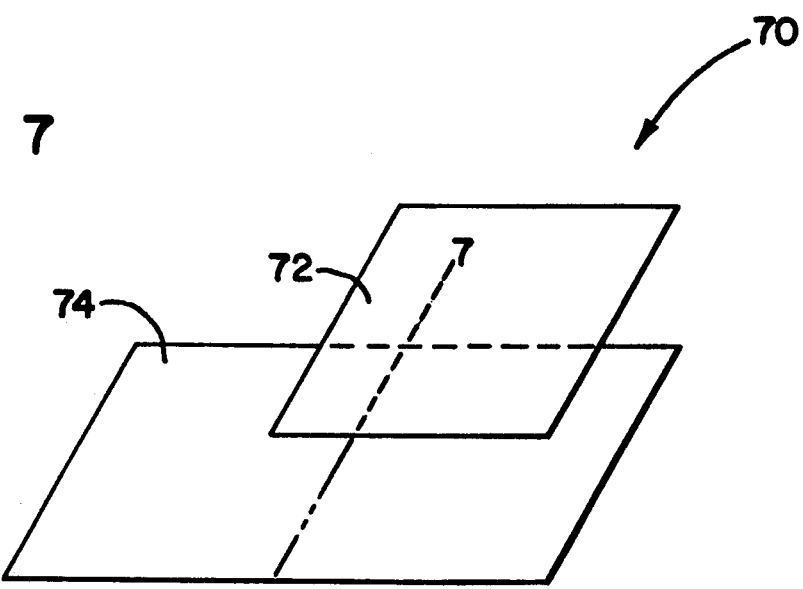
FIG. 7 is an exploded diagrammatic view which shows top and bottom sheets of material used to make an embodiment of the invention shown in FIGS. 8 and 9.
Figure 8:
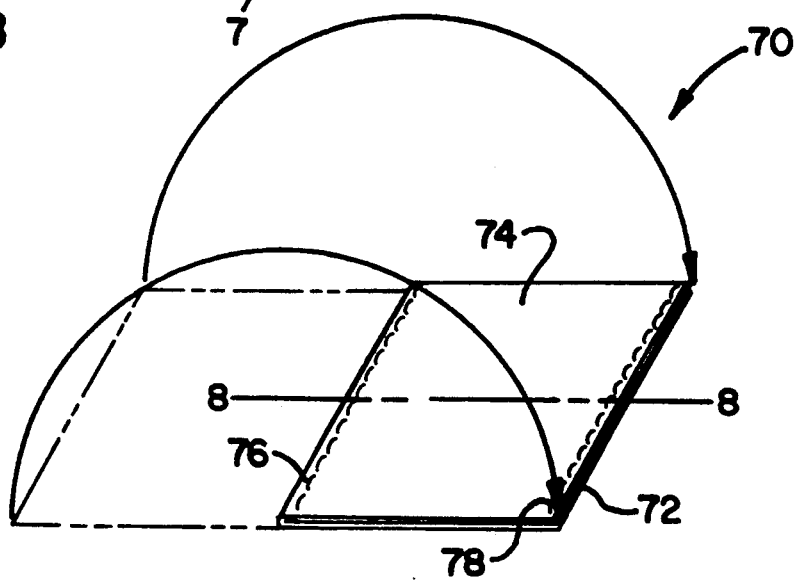
FIG. 8 shows the bottom sheet of material shown in FIG. 7 being folded over the bottom sheet to a first position comprising three layers.
Figure 9:
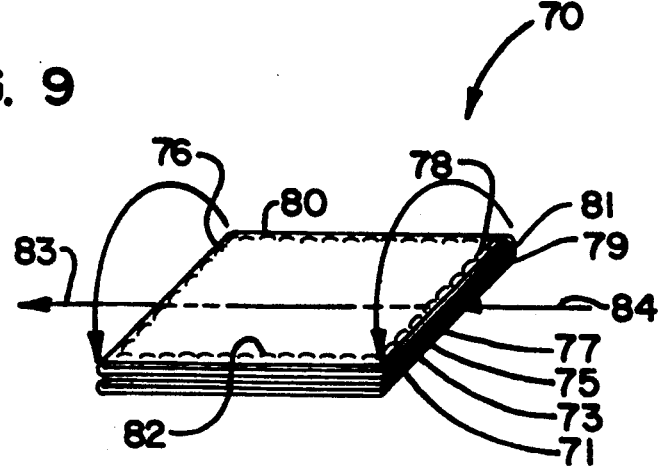
FIG. 9 shows the three layers of FIG. 8 being folded to a second position comprising six layers.

Referring now to the drawings, FIGS. 7, 8 and 9 show an alternative embodiment, diaper 70, made according to the present invention. The diaper 70 comprises six layers 71, 73, 75, 77, 79 and 81. These six layers are made from two sheets of material 72 and 74 as shown in FIG. 7. In the preferred embodiment, sheet 72 is half the size of sheet 74. Sheet 72 is preferably made from a more absorbent material such as terry cloth or the like. In the preferred embodiment, sheet 72 is made from a woven or knit material or the like.

FIG. 8 shows that sheet 74 is folded along line 7—7 to form three layers.

It should be noted that FIG. 8 also shows another embodiment of the present invention. This embodiment may be made with discontinuous perimeter closure as shown or continuous perimeter closure. In the preferred embodiment, stitching or attachment means 76 and 78 are provided. Stitching 78 provides closure between the three layers along the line defined by stitching 78. It should be noted that stitching 76 is not needed to provide closure along the line defined by stitching 76. Rather, closure between the three layers shown in FIG. 8 is already provided by the fold along lines 7—7 in sheet 74. Stitching 76, however, helps to secure the layers so that, for example, during the washing of the diaper, the internal layers do not get crumpled or misaligned.

FIG. 9 shows that the layers in FIG. 8 are folded to define the six layers of the diaper 70. Stitching or attachment means 80 and 82 are provided in the preferred embodiment.

Accordingly, in the preferred embodiment, continuous perimeter closure is provided between layers 71 and 73; 73 and 75; 77 and 79; and 79 and 81 by stitching 72, stitching 82, stitching 76 (or fold along line 7—7), and stitching 80 (or fold along line 8—8). Discontinuous perimeter closure is provided between layers 75 and 77. In the preferred embodiment apertures 83 and 84 are defined between layers 75 and 77. Apertures 83 and 84 permit air to flow through the center of the diaper 70.

FIGS. 10 and 11 show another alternative embodiment of the present invention. This embodiment comprises six layers made from three sheets of material 86, 87 and 88. Preferably, sheet 86 is made from a more absorbent material. In the preferred embodiment, stitching or attachment means 94, 92 and 90 are provided. Sheets 86, 87 and 88 are folded along line 10—10 to define six layers. In the preferred embodiment, stitching 96 is provided. Accordingly, apertures 98 and 99 are defined between the middle two layers. Continuous perimeter closure is provided between the remaining layers in the preferred embodiment as shown.

In other embodiments of the diaper 85, stitching or attachment means could be provided to define at least one opening between each of the layers. For example, stitching 90 and 92 could be eliminated thus defining an opening between each layer.

It should be noted that a four layer diaper may be constructed in a similar manner as shown in FIGS. 10 and 11. For example, it could be accomplished by eliminating one of the sheets of material 86, 87 or 88.

FIGS. 12 and 13 show an alternative embodiment of the present invention. Diaper 100 comprises three layers made from a single sheet 102. Sheet 102 is first folded as shown in FIG. 12. In the preferred embodiment, stitching 104 and 105 is provided. However, stitching 104 and 105 is not necessary. Sheet 102 is again folded as shown in FIG. 13. In the preferred embodiment, stitching 106 and 108 is provided. Accordingly, apertures 110 and 111 are defined between the top two layers. In the embodiment which eliminates stitching 104 and 105, apertures would be provided between each of the layers in diaper 100. It should be noted that sheet 102 could also be folded accordion style.

It is to be understood that, even though numerous characteristics and advantages of the present invention have been set forth in the foregoing description, together with details of the structure and function of the invention, the disclosure is illustrative only, and changes may be made in the detail, especially in matters of shape, size and arrangement of parts within the principles of the invention to the full extent indicated by the broad and general meaning of the terms in which the appended claims are expressed.

What is claimed is:

1. A reusable diaper comprising:
   at least three layers having respective first and second ends;
   continuous closure means for providing continuous closure between a first two adjacent layers along their respective first and second ends;
   discontinuous closure means for providing discontinuous closure between a second two adjacent layers along their respective first and second ends, the discontinuous closure means defining at least one opening between the second two adjacent layers, the opening permitting air to more freely enter and flow between the layers and thereby permit the diaper to dry faster.

2. A reusable diaper according to claim 1 wherein the layers are made from two sheets of material arranged to define the layers, wherein at least one of the sheets of material is folded.

3. A reusable diaper according to claim 1 comprising six layers, wherein the six layers are made from two sheets of material folded to define six layers.

4. A reusable diaper according to claim 1 comprising four layers, wherein the four layers are made from two sheets of material folded to define four layers.

5. A reusable diaper according to claim 1 comprising six layers, wherein the six layers are made from three sheets of material folded to define six layers.

6. A reusable diaper according to claim 1 comprising three layers, wherein the three layers are made from a single sheet of material folded to define three layers.

7. A reusable diaper comprising:

three layers, each of the layers having first and second opposite ends, first and second opposite sides, and interior surfaces, each of said opposite sides and opposite ends having an outer edge;

said layers being attached continuously along said outer edges of said opposite sides;

wherein said outer edges of only one of said first and second opposite ends is free from any attachment means and the interior surfaces of the respective layers are free from any attachment means so that during use a smoother and more comfortable fit is provided and so that during a cleaning and drying cycle air is more freely able to flow between the interior surfaces of the respective layers, permitting the diaper to dry faster; and wherein the three layers are made from two sheets of material.

8. A reusable diaper comprising:

six layers, each of the layers having first and second opposite ends, first and second opposite sides, and interior surfaces, each of said opposite sides and opposite ends having an outer edge;

said layers being attached continuously along said outer edges of said opposite sides;

wherein said outer edges of only one of said first and second opposite ends is free from any attachment means and the interior surfaces of the respective layers are free from any attachment means so that during use a smoother and more comfortable fit is provided and so that during a cleaning and drying cycle air is more freely able to flow between the interior surfaces of the respective layers, permitting the diaper to dry faster; and wherein the six layers are made from two sheets of material folded to define six layers.

* * * * *